(12) United States Patent
Marshall et al.

(10) Patent No.: US 11,085,065 B2
(45) Date of Patent: Aug. 10, 2021

(54) PHENOTYPIC ENGINEERING OF SPORES

(71) Applicant: M. Boris Rotman, Phoenix, AZ (US)

(72) Inventors: Mindy A. Marshall, Warwick, RI (US); Linda M. Olmsted, North Kingstown, RI (US); M. Boris Rotman, Phoenix, AZ (US)

(73) Assignee: M. Boris Rotman, Phoenix, AZ (US)

( * ) Notice: Subject to any disclaimer, the term of this patent is extended or adjusted under 35 U.S.C. 154(b) by 285 days.

(21) Appl. No.: 15/627,415

(22) Filed: Jun. 19, 2017

(65) Prior Publication Data

US 2017/0292143 A1 Oct. 12, 2017

Related U.S. Application Data

(63) Continuation-in-part of application No. 11/708,829, filed on Feb. 21, 2007, now abandoned.

(60) Provisional application No. 60/775,252, filed on Feb. 21, 2006.

(51) Int. Cl.
| | |
|---|---|
| *C12Q 1/22* | (2006.01) |
| *C12N 3/00* | (2006.01) |
| *C12Q 1/04* | (2006.01) |
| *C12N 1/20* | (2006.01) |
| *C12N 1/00* | (2006.01) |

(52) U.S. Cl.
CPC .................. *C12Q 1/22* (2013.01); *C12N 1/20* (2013.01); *C12N 3/00* (2013.01); *C12Q 1/04* (2013.01); *C12N 1/00* (2013.01); *C12Q 2304/00* (2013.01); *G01N 2333/32* (2013.01)

(58) Field of Classification Search
None
See application file for complete search history.

(56) References Cited

U.S. PATENT DOCUMENTS

| | | | | |
|---|---|---|---|---|
| 5,073,488 A | * | 12/1991 | Matner .................... | C12Q 1/22 435/31 |
| 5,770,393 A | * | 6/1998 | Dalmasso ................ | C12Q 1/22 435/22 |

OTHER PUBLICATIONS

Guibault et al. Analytical Biochemistry, 1966, 14(1), pp. 28-40; STN abstract accession No. 1966:37316 CAPLUS.*
Vepachelu et al. FEMS Microbiology Letters, 2004, 239, pp. 71-77.*

* cited by examiner

*Primary Examiner* — Vera Afremova
(74) *Attorney, Agent, or Firm* — Olav M. Underdal; IDP Patent Services (57) ABSTRACT

The biological functionality of living microbial spores is modified using phenotypic engineering to endow the resulting modified spores with novel functionality that extends the usefulness of the spores for a variety of practical applications including, for example, sterility testing, the release of active compounds, and cell-based biosensing systems. An embodiment entails engineering *Bacillus* spores to acquire synthetic new functions that enable the modified spores to sense and rapidly transduce specific germination signals in their surroundings. The newly acquired functions allow the spores to perform, for example, as self-reporters of cellular viability, self-indicating components of cell-based biosensors, and in other analytical systems. Also disclosed are methods for testing adequate sterility of a system by using engineered spores.

15 Claims, 2 Drawing Sheets

PHENOTYPIC ENGINEERING OF SPORES

CROSS-REFERENCE TO RELATED APPLICATIONS

This United States Non-Provisional application is a continuation-in-part of U.S. Non-Provisional application Ser. No. 11/708,829, filed Feb. 21, 2007, which claims the benefit of U.S. Provisional Application No. 60/775,252, filed Feb. 21, 2006.

FIELD OF THE INVENTION

The present invention relates generally to the field of phenotypic engineering of spores, and more particularly to methods and systems for the preparation of modified spores useful in the fields of biological and biochemical indicators, most particularly those used for a variety of assays including bio-sensing and sterility testing

BACKGROUND OF THE INVENTION

Sterility Testing

In many industries, sterilization processes are routinely used to kill microorganisms that may contaminate food, beverages, solutions, equipment or devices. Different techniques may be used for sterilizing including steam autoclaving for about 3 to 60 minutes at temperatures ranging from about 110° C. to 132° C., dry heating for 30 or more minutes at 150° C. to 160° C., and exposure to radiation or chemicals such as ethylene oxide, vaporized hydrogen peroxide, and peracetic acid.

For most processes, it is critical to monitor the effectiveness of the equipment and procedure used for sterilizing. For example, it is standard practice in medical and pharmaceutical institutions to use an indicator for sterility assurance to ascertain that no living microorganisms are present in materials that have undergone a sterilization process. Over the years, different types of sterility indicators have been developed including biological and chemical indicators.

While chemical indicators are often used to monitor gross failures of sterilization processes, it is well recognized in the art of sterilization that biological indicators consisting of living microbial spores are one of the most accurate and reliable systems for sterility assurance. Microbial spores are preferred over vegetative cells because spores are more resistant to physical and chemical treatments. A traditional method for sterility testing is to place a carrier with spores near the items to be sterilized, and after sterilization, to detect any surviving spores by incubating the spores in a bacteriological growth medium. Spore outgrowth after incubation periods ranging from one to seven days is taken as an indicator of inadequate sterilization. A major disadvantage associated with this method is that seemingly sterilized articles must be stored for prolonged times until test results become available.

In the last two decades, efforts to develop faster methods for monitoring sterility have been directed at techniques in which bacterial enzymes, either present in or extracted from vegetative cells, are substituted for the traditional biological indicators based on outgrowth of microbial spores. For example, an enzyme-based sterility indicator is disclosed in U.S. Pat. No. 5,073,488 (Matner et al.), and indicator systems using several different enzymes and their respective substrates have also been described in U.S. Pat. No. 5,486,459 (Burnham et al.). Typically, in the enzyme-based technology, a carrier with a particular enzymatic activity is placed near the items to be sterilized, and after sterilization, the remaining enzymatic activity is determined by incubating the indicator with a specific substrate yielding detectable product(s). The amount of remaining enzymatic activity is used as a parameter to assess the efficacy of the sterilization process. Thus, the reliability of this type of enzyme-based indicators hinges on the implicit assumption that the rate of enzyme inactivation correlates accurately with the rate of spore killing. Consequently, using this type of indicator, inadequate sterilization is indicated by partial enzyme inactivation or no enzyme inactivation. However, and most importantly, complete enzyme inactivation is not a reliable sterility assurance test because enzymes may be prematurely inactivated in comparison to spore killing. Diverse efforts to circumvent the problem of premature enzyme-inactivation have been described. For example, spores or the source of active enzyme may be chemically treated to enhance the resistance of the enzyme to premature inactivation as described in U.S. Pat. No. 7,045,343 (Witcher et al.). The chemicals described in that patent typically include surfactants, waxes, and oils such as polyglycerol alkyl esters and ethoxylated glycerol esters.

For these reasons, enzyme-based indicators do not provide the same type of sterility assurance obtained with traditional indicators based on measuring outgrowth of surviving spores. In this respect, enzyme-based indicators resemble chemical indicators in that both can only indicate gross failures of the sterilization equipment or process.

Another drawback of enzyme-based indicators is that the amount of enzyme present in the indicator system has to be carefully calibrated to ensure that the rate of enzyme inactivation in fact correlates with the rate of spore killing. However, calibrating enzymatic activity is not a simple procedure, since it depends on a number of parameters such as enzyme concentration, enzyme purity, and incubation temperature. The problems associated with calibrating enzymatic activity are compounded when using either crude enzyme preparations or microbial spore preparations that usually contain relatively large concentrations of enzymes from vegetative cells contaminating the preparations. For example, preparations of *G. stearothermophilus* spores are normally contaminated with 5-20% of vegetative cells. Moreover, it is common that enzymes lose activity during purification, a fact that makes difficult to calibrate the activity of the enzyme in the indicator.

In efforts to circumvent the aforementioned problems associated with enzyme-based indicators, dual systems have been recently introduced in which an enzyme-based indicator for early warning is used in combination with a traditional indicator based on spore outgrowth. For example, an invention using a dual system is disclosed in U.S. Pat. No. 5,418,167 (Matner et al.) which describes a sterility indicator (termed a biological indicator, which can also be referred to as a self-contained biological indicator) that contains in separate compartments a strip with *Geobacillus stearothermophilus* spores that have detectable alpha-glucosidase activity; growth medium; and 4-methylumbelliferyl-alpha-D-glucoside, a fluorogenic substrate of alpha-glucosidase. After sterilization, the spores, the growth medium, and the substrate are mixed together and incubated. Following 2-4 hours of incubation, the presence of alpha-glucosidase activity (detected by an increase in fluorescence) indicates inadequate sterilization. On the other hand, if enzymatic activity is undetectable after four hours of incubation, the indicator is further incubated for one or several days in order to detect outgrowth of any surviving spores. Consequently, this type of combination indicator system does not represent an improvement over traditional biological indicators since it still requires several days to provide reliable sterility assurance.

Another type of enzyme-based sterility indicator is disclosed in U.S. Pat. No. 5,770,393 (Dalmasso et al.). It uses enzyme production during outgrowth of surviving spores as a method to increase assay sensitivity and thereby reduce assay time. For example, alpha-amylase activity produced by vegetative cells is indicative of spore outgrowth in the indicator and may be detected after 2-8 hours of incubation using a specific alpha-amylase substrate. This type of indicator system, however, does not have the single-spore sensitivity of conventional biological indicators based on measuring spore killing by spore outgrowth.

Also, enzyme production by genetically engineered spores is described in U.S. Pat. No. 8,372,264 (Phillip P. Franciskovich et al), which describes a genetically engineered biological indicator, wherein the engineered spores produce an enzyme during a 2-4 hour outgrowth.

Although it is traditional to monitor sterilization processes using spore outgrowth as the "viability parameter", other cellular activities closely related to spore viability have also been used as parameters of cell survival. For example, U.S. Pat. No. 5,795,730 (Tautvydas) discloses that certain biological reactions, such as loss of refractivity occurring during spore germination, may be used to measure the effectiveness of sterilization processes. Spore germination is a complex, irreversible process consisting of many different reactions (most of them still unknown) triggered when microbial spores encounter outgrowth chemical conditions. Germination is independent of transcriptional control and includes two sequential stages: Stage I and Stage II, as described in P. Setlow, "Spore Germination," Current Opinion in Microbiology, Vol 6, p 550-6 (2003). Particularly, Setlow describes that spore outgrowth solely takes place after the two stages of spore germination.

Stage II ensues when the activated spore encounters a germinant (e.g., amino acids, adenosine, and glucose). It is during Stage II that the spore undergoes irreversible changes including increased outer coat permeability that allow both influx of nutrients and water into the cell and efflux of cellular components. In addition, some time during Stage II the spore loses its heat resistance and refractivity. The outgrowth stage is characterized by spores returning to their vegetative cell morphology and functions. In contrast to the outgrowth stage which necessitates de novo synthesized cellular components, both the first and second stages of germination use only preformed components. Since germination is a vital process preceding spore outgrowth, sterilization conditions resulting in complete loss of a spore's ability to germinate will generally indicate adequate sterilization.

A commonly used method to determine germination in a spore suspension is based on loss of light scattering properties due to biochemical changes in the spore's wall. U.S. Pat. No. 5,795,730 (Tautvydas) discloses a method to rapidly measure the effectiveness of sterilization processes by determining the rate of spore germination after sterilization using a loss of light scattering as the parameter. The drawbacks of this method are that it is labor intensive and difficult to automate. Also, the sensitivity of the method is considerably lower than that of traditional testing by spore outgrowth.

In various aspects, the present invention discloses novel biological indicator systems for sterility assurance based on phenotypic engineered spores that have capabilities as self-reporters of germination. Therefore, the engineered spores have unique functionality as compared to normal spores currently used as biological indicators for sterility testing.

Cell-Based Biosensing

Living microbial spores have been previously used as sensing components in devices for detecting and identifying bacterial cells, including pathogenic microorganisms, macromolecules and other analytes directly from a test sample. In these systems, the spores were used to sense specific signals from analytes and to respond to them by establishing an analyte-independent signal amplification system. For example, U.S. Pat. No. 6,596,496 (Rotman) discloses methodologies that provide a particularly efficient technique to conduct thousands of parallel assays in an array of microscopic biosensors. These methodologies teach a label-free (label-less), growth-independent, analytical system (termed "LEXSAS™") using enzyme-free spores for rapid detection and identification of different analytes directly from a test sample. In that invention, the test material is mixed with a germinogenic substrate and enzyme-free spores prepared from selected bacterial strains. The mixture is allowed to stand for a short period of time to permit analyte-induced generation of germinant from the germinogenic substrate. The newly formed germinant triggers spore germination and subsequently by de novo synthesis of enzyme capable of producing additional germinant from the germinogenic substrate. The newly formed germinant promotes further spore germination with concomitant de novo enzyme synthesis that results in a propagating cascade of analyte-independent germination. The end point of the cascade can be measured using an assortment of physical and conventional enzymatic methodologies, e.g., hydrolysis of chromogenic or fluorogenic substrates.

In various aspects, the present invention serves to improve previously developed biosensors by utilizing phenotypic engineered spores that have self-reporting capabilities and therefore can function more efficiently than the previous normal spores, i.e. naturally occurring non-engineered spores, that have been used in various biosensing devices.

Spores have previously been genetically engineered to produce an immune response to an antigen, c.f. U.S. Pat. No. 5,800,821 (Acheson et al.), which discloses a method of stimulating a vertebrate animal to produce an immune response to at least one antigen. The method includes genetically engineering a bacterial cell with DNA encoding at least one antigen and inducing the bacterial cell to sporulate, then orally administering the bacterial spores to an animal. The bacterial spores germinate in the gastrointestinal tract of the animal and express the antigen so that it comes into contact with the animal's immune system and elicits an immune response.

U.S. Pat. No. 5,766,914 (Deits) discloses a method of producing and purifying an enzyme by selecting a spore forming host organism, preparing a genetic construct consisting of a DNA sequence encoding a desired enzyme and a DNA sequence directing synthesis of the desired enzyme during sporulation, inserting the genetic construct into the host organism, culturing the transformed host organism under sporulating conditions to obtain host organism spores with the enzyme integrally associated to the spores, and then treating the host organism and enzyme combination to remove any impurities, if necessary. The free enzyme can be obtained by cleaving the connection between the host organism and the enzyme. The combination of the enzyme and host organism is both a stabilized and an immobilized enzyme preparation.

As such, considering the foregoing, it may be appreciated that there continues to be a need for novel and improved devices and methods for sterility testing, biosensing, and testing of other biological and biochemical properties.

SUMMARY OF THE INVENTION

The foregoing needs are met, to a great extent, by the present invention, wherein in aspects of this invention, enhancements are provided to the existing models of sterility testing, biosensing, and testing of other biological and biochemical properties.

In various aspects, this invention is directed to a phenotypically engineered spore that includes man-made structure and functionality under the control of the spore's natural germination apparatus, to give the spore self-reporting capability. The man-made functionality is introduced by contacting the spores with a hydrophobic compound. Suitable such functionalities can include fluorogenicity, chromogenicity, chemiluminogenicity, bioluminogenicity, and indigogenicity.

In related aspects, this invention relates to novel methodologies that utilize phenotypic engineering to modify the performance of living spores as rapid and rugged indicators of environmental changes. An example of such methodologies is the phenotypic engineering of living *Bacillus* spores to create a new function enabling the spores to perform as fluorogenic biological microorganisms. The new fluorogenic functionality is advantageous for determining susceptibility of microbial spores to sterilization conditions and other chemical and physical treatments.

In another aspect, the present invention is directed to procedures, devices and kits for phenotypically engineering living spores for the purpose of creating engineered spores so as to have man-made structures and functionalities not previously observed in nature. The invention allows to manipulates spores as chemically inert particles suspended in organic solvents while still maintaining their ability to germinate as normal spores.

More particularly, aspects of the present invention are directed to phenotypically engineered spores that includes a man-made functionality under the control of the spore's natural germination apparatus to give the spore self-reporting capability. The man-made functionality is introduced by contacting the spores with a hydrophobic compound which has a visual generating property, such as: fluorogenicity, chromogenicity, chemiluminogenicity, bioluminogenicity, or indigogenicity.

In related aspects, the invention makes available different embodiments to obtain phenotypically engineered spores useful for sterility testing and for delivering signals that can be used for detecting and identifying particulate analytes such as microbial cells, viruses, and biological macromolecules such as antibodies, cytokines, nucleic acids (DNA and RNA) and proteins.

In an aspect, a method of using engineered spores to test adequacy of a sterilization process for a system, can include:

a) obtaining the engineered spores;

b) adding the engineered spores to the system;

c) sterilizing the system, wherein the system with the engineered spores is subjected to the sterilization process;

d) exposing the engineered spores to a germinant for a predetermined germination period; and e) measuring fluorescence, wherein the fluorescence of the engineered spores is measured to obtain a fluorescence measurement;

such that a substantially zero fluorescence response indicates that the sterilization process is adequate, and a fluorescence substantially above zero response indicates that the sterilization process is inadequate;

wherein the engineered spores each comprise:

a first spore; and an at least partially hydrophobic compound, which is incorporated into the first spore;

wherein the at least partially hydrophobic compound is fluorogenic, such that the at least partially hydrophobic compound is configured to become fluorescent by hydrolysis;

wherein the only fluorogenic compound in the engineered spores is the at least partially hydrophobic compound that is incorporated into the first spore in each of the engineered spores;

wherein the engineered spore, which can also be referred to as a phenotypically engineered spore, is configured to be capable of germination; and wherein the engineered spore is non-fluorescent;

wherein the engineered spore does not comprise a germinant;

such that the engineered spore is configured to become fluorescent upon germination.

In a related aspect, the at least partially hydrophobic compound can be hydrophobic or amphiphilic.

In a related aspect, the at least partially hydrophobic compound can be dipropionylfluorescein.

In another related aspect, the at least partially hydrophobic compound can be diacetyl fluorescein.

In yet a related aspect, the at least partially hydrophobic compound can be dibutyryl fluorescein.

In a related aspect, the at least partially hydrophobic compound can be SYTO 9.

In a related aspect, the first spore can be a spore of *Geobacillus stearothermophilus*.

In a related aspect, the first spore can be a spore of *Bacillus cereus*.

In a related aspect, the first spore can be a spore of *Bacillus atrophaeus*.

In a related aspect, the first spore can be a spore of *Bacillus megaterium*.

In another aspect, a sterilization testing method for testing the adequacy of a sterilization process by using an engineered spore suspension, can include:

a) obtaining the engineered spore suspension;

b) sterilizing the engineered spore suspension, wherein the engineered spore suspension is subjected to the sterilization process;

c) incorporating a germinant into the sterilized engineered spore suspension;

d) waiting for a predetermined germination period; and e) measuring fluorescence, wherein the fluorescence of the sterilized engineered spore suspension is measured to determine if there is a fluorescence signal;

whereby a substantially zero fluorescence signal indicates that the sterilization process is adequate, and a fluorescence signal substantially above zero indicates that the sterilization process is inadequate;

wherein the engineered spore suspension comprises:
a sterile liquid solution; and
a plurality of engineered spores, wherein each engineered spore comprises:
a first spore; and
an at least partially hydrophobic compound, which is incorporated into the first spore;
wherein the plurality of engineered spores is suspended in the sterile liquid solution;
wherein the at least partially hydrophobic compound is fluorogenic, such that the at least partially hydrophobic compound is configured to become fluorescent by hydrolysis;
wherein the only fluorogenic compound in the engineered spore suspension is the at least partially hydrophobic compound that is incorporated into the first spore of each engineered spore;
wherein the engineered spores are configured to be capable of germination; and wherein the engineered spores are non-fluorescent;
wherein the engineered spore suspension does not comprise a germinant;
such that the engineered spores are configured to become fluorescent upon germination.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 1 is a flowchart illustrating steps that may be followed, in accordance with one embodiment of a method or process of using engineered spores to test adequacy of a sterilization process for a system.

FIG. 2 is a flowchart illustrating steps that may be followed, in accordance with one embodiment of a sterilization testing method or process for testing the adequacy of a sterilization process using an engineered spore suspension.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

For purposes of clarity of disclosure, the following dictionary of terms shall apply, such that:

a) "Engineered" denotes a property of having additional structure or functionality added or created according to a human process of engineering, in contrast to non-engineered structures, compounds or organisms found in nature;

b) "Fluorescent" denotes a property of emitting light at an emission wavelength after absorption of light at an absorption wavelength, which is usually shorter than the emission wavelength;

c) "Flourogenic" denotes a property of having an inherent capability of generating fluorescence upon a specific activation, such as hydrolysis or enzymatic action;

d) "Chromogenic" denotes a property of having an inherent capability of generating a color upon a specific activation, such as hydrolysis;

e) "Chemiluminogenic" denotes a property of having an inherent capability of generating light upon a specific activation that involves a chemical process;

f) "Bioluminogenic" denotes a property of having an inherent capability of generating light upon a specific activation that involves a biochemical or biological process; and g) "Indigogenic" denotes a property of having an inherent capability of generating insoluble indigo blue upon a specific activation, such as hydrolysis.

In various embodiments, the present invention relates to the preparation and practical applications of phenotypic engineered spores in which a man-made structure and functionality has been introduced and placed under control of the spore's natural germination apparatus. Thus, in general, an engineered spore, is a natural spore that has been modified to incorporate additional structure that is not normally present in spores found in natures, such that the additional structure has an inherent functionality, which can be activated, for example as a consequence of spore germination.

In related embodiments, this invention further relates to sterility testing utilizing the phenotypic engineered spores as self-indicators of adequate sterilization conditions, wherein the man-made functionality of these spores can be chromogenic, fluorogenic, chemiluminogenic, bioluminogenic, or indigogenic.

In other further related embodiments, the invention further relates to biosensing to detect analytes through the use of phenotypic engineered microbial spores acting as both signal-sensors and signal-transducers of analyte-specific signals. An analyte is detected by placing a sample suspected of containing the analyte in a mixture of phenotypic engineered spores and a germinogenic source. The end result is a detectable signal, such as bioluminescence, color, or fluorescence that can be used to determine the presence, location, and number of discrete entities of analytes.

In yet other further related embodiments, this invention further relates to test kits containing the phenotypic engineered spores.

In related embodiments, the phenotypically engineered spores of this invention are produced by suspending living spores in a liquid, contacting the suspended spores with a hydrophobic compound under conditions which cause the hydrophobic compound to incorporate and self-assemble into the spores to form modified spores, which are washed twice with a cold sterile aqueous solution and resuspended in a cold aqueous solution, which thereby forms a suspension of engineered spores.

More particularly, in a first embodiment of this invention, the phenotypic engineered spores can be prepared from dried living spores containing less than about 5% extracellular water. The dried spores are suspended in a non-aqueous solution containing a selected hydrophobic molecular probe similar to those listed in Table 1. The resulting spore suspension is incubated for a sufficient period of time to allow incorporation and self-assembling of the selected hydrophobic molecular probe in the spores. Finally, the organic solvent is removed, for example under vacuum.

The living spores engineered according to this method not only remain viable, but also become self-reporters of germination. Accordingly, the engineered spores are suitable for using as direct biological indicators or as components of cell-based biosensing devices.

In relation to the foregoing, a self-reporting capability of an engineered spore shall be understood to be a capability such that a self-reporting engineered spore, which is a spore comprising a self-reporting structure, is configured to emit a reporting/indicator signal when the self-reporting engineered spore is exposed to an environment containing a stimulant. Thus, for example, a fluorogenic engineered spore can have a self-reporting function for germination, wherein the fluorogenic engineered spore is configured to become fluorescent when the fluorogenic engineered spore is exposed to an environment containing a germinant (stimulant) and consequently germinates.

The dried spore preparation (before engineering) may be prepared by different well-known procedures. A typical procedure entails heat-activating a spore suspension in sterile deionized water at a temperature of about 50 to 110° C. for about 5 to 60 minutes, for example, 65° C. for about 30 minutes, and then spinning the suspension at 10,000×g for about 5 minutes to pellet the spores and form a supernatant. After removal of the supernatant, the pellets can be dried under vacuum for about 90 to 120 minutes over a desiccant such as silica gel. The dried spores should contain less than about 5% extracellular water, including for example less than about 1%.

Appropriate organic solvents for preparing the non-aqueous suspensions include chemicals such as acetone, acetonitrile, ethyl acetate, methyl ethyl ketone, tetrahydrofuran, and toluene. The spore suspension may be formed by pipetting up-and-down the dried spores with the non-aqueous solution containing the selected molecular probe to be engineered into the spores. The engineered spores using this methodology were experimentally shown to have acquired a man-made function controlled by the spore's innate germination apparatus. This unexpected result probably stems from the fact that the hydrophobic molecular probes self-assemble forming a discrete boundary around the spore's outer coat (as determined by ultrathin cryo-sectioning and imaging under an electron microscope).

In a second embodiment of this invention, phenotypic engineered spores can be prepared by a simpler procedure, in which living spores suspended in sterile buffer solution are contacted with a particular hydrophobic chemical dissolved in an amphiphilic solvent such as acetone, N,N-dimethylformamide, dimethylsulfoxide, and N,N-dimethylacetamide. For spore engineering, 200 μL of a heat-activated spore suspension is rapidly mixed with 5 μL of a solution containing a selected hydrophobic molecular probe similar to those listed in Table 1, and the mixture is incubated at non-deleterious conditions, for example, at room temperature for 10-15 min with occasional shaking. Alternatively, the mixture may be incubated at 0° C. for 30 minutes. After incubation, the engineered spores are washed twice with a cold sterile aqueous solution and resuspended in a cold aqueous solution.

In a third embodiment of this invention, phenotypic engineered spores can be prepared from living spores suspended in sterile, deionized water. The spores are then contacted with a fine emulsion of a hydrophobic molecular probe under conditions that favor apolar (hydrophobic) binding of the selected biochemical to the spores. Fine emulsions of hydrophobic molecular probes may be easily produced as illustrated by the following example using diacetyl fluorescein (DAF) to engineer spores. An emulsion is prepared by mixing 0.5 mL of an acetone solution containing 0.5 mg/mL DAF with 0.5 mL deionized water. For spore engineering, about 1.0 mL, of the emulsion is mixed with about 50 μL of a heat-activated spore suspension and the mixture is incubated at room temperature for about 10 minutes with occasional shaking. After incubation, the spores are washed, generally twice, in cold buffer. The resulting spores can be experimentally shown to have acquired a manmade, fluorogenic functionality placed under control of the germination machinery of the spore. That is, the engineered spores of this invention are not fluorescent by themselves, but rapidly respond to the presence of germinants in their immediate environment by producing bright green fluorescent light.

In a fourth embodiment, phenotypic engineered spores can be prepared from microbial spores that have been previously committed to germinate by contacting them to a specific germinant for 1-3 minutes. Commitment is considered a measure of the first irreversible reaction preceding germination and spore outgrowth into a vegetative bacterium (Gordon, S. A. et al. (1981) Commitment of bacterial spores to germinate. Biochem. J. 198:101-106. Setlow, P. (2003) Spore Germination. Curr. Opinion Microbiol. 6: 550-556). Since committed spores behave differently than normal spores in many important respects, phenotypic engineered spores prepared from committed spores can find novel, practical applications in the recent field of spore-based biosensing (U.S. Pat. No. 6,872,539, Rotman). For example, we discovered that committed spores respond differently to environmental signals and also that they have different germinant specificity than normal (not committed) spores. A particularly striking illustration of this discovery is our observation that D-alanine, a well-known competitive inhibitor of L-alanine-induced germination for many bacterial spores (Moir, A. and Smith, D. A. 1990. The genetics of bacterial spore germination. Annu. Rev. Microbiol. 44: 531-53), becomes an efficient inducer of germination for committed spores and also for phenotypic engineered committed spores constructed according to embodiments of this invention.

An embodiment useful for using the invention as biological indicator for sterility testing is to use spores dried in appropriate matrices commonly used in the sterility testing industry such as strips or disks of filter paper. After the spores have been subjected to a sterilization process, they are converted to phenotypic engineered spores directly in the matrix (i.e., in situ). This embodiment is applicable for example when using phenotypic engineered spores as biological indicators for testing steam-based sterilizers such as autoclaves, that may release molecular probes from the engineered spores.

Some example of the types of molecular probes suitable for preparing phenotypic engineered spores according to embodiments of this invention are shown in Table 1. The compounds listed in the table are representative of hydrophobic chemicals suitable for use in the present invention, but are not the only such compounds useful herein. It should also be noted that molecular probes suitable for the invention can have diverse functionalities. For example, some molecules can be enzyme substrates while others can be molecules that become bioluminescent or fluorescent when forming complexes with ions (such as calcium, magnesium, and iron), nucleic acids (such as DNA and RNA), or proteins (such as luciferase). A person of normal skill in the art will be able to determine without too much experimentation the type of molecular probe suitable for constructing phenotypic engineered spores, according to embodiments of this invention.

TABLE 1

| Molecular Probes Suitable for Phenotypic Engineering of Spores | |
|---|---|
| | Engineered Synthetic Functionality |
| Fluorogenic probes (e.g. enzyme substrates) | Engineered spores transduce external germination signals into fluorescent signals |
| Fluorogenic probes (e.g., nucleic acid stains) | Engineered spores transduce external germination signals into fluorescent signals through DNA/RNA binding |
| Fluorogenic probes (e.g., calcium probes) | Engineered spores transduce external germination signals into fluorescent signals through calcium binding |
| Chromogenic probes (e.g. pH indicators) | Engineered spores transduce external germination signals into colored signals |
| Chemoluminescence probes | Engineered spores transduce external germination signals into chemo-luminescent signals |
| Bioluminescence probes | Engineered spores transduce external germination signals into bioluminescent signals |
| Indigogenic probes | Engineered spores transduce external germination signals into insoluble indigo dyes |
| Quantum Dots | Engineered spores release quantum dots when exposed to external germination signals |
| Hydrophobic, biologically active compounds | Engineered spores release biologically active compounds when exposed to external germination signals |

The usefulness of various embodiments of the present invention is illustrated by the following test for detecting coliform bacteria (the analyte) in a sample. For this practical test, the phenotypic engineered spores can be engineered according to the present invention to be fluorogenic by incorporating dipropionylfluorescein in the spores and allowing it to interface with the spore's germination apparatus. The engineered spores are able to detect the analyte because most coliforms have β-D-galactosidase (EC 3.2.1.23), also known as lactase, an enzyme used as a specific marker for fecal contamination of environmental waters. The test system consisted of a buffer solution with the following additions:
  (A) Engineered, fluorogenic spores of *B. megaterium*, strain QM B1551.
  (B) Lactose, a germinogenic substrate releasing D-glucose (a potent, specific germinant of *Bacillus megaterium* spores) when hydrolyzed by β-D-galactosidases.

Under appropriate pH and temperature conditions (e.g., pH 6.8-7.8 and 20° C. to 40° C.) coliform bacteria containing β-D-galactosidase produce D-glucose (from lactose hydrolysis) which, in turn, triggers spore germination and concomitant fluorescence due to hydrolysis of dipropionylfluorescein integrated into the spores. The fluorescence produced in the system is measured using standard fluorometry.

The components and reagents for engineering spores according to the present invention may be supplied in the form of a kit in which the simplicity and sensitivity of the methodology are preserved. All necessary reagents can be added in excess to accelerate the reactions. In some embodiments, the kit can also comprise a preformed biosensor designed to receive a sample containing an analyte. The exact components of the kit will depend on the type of assay to be performed and the properties of the analyte being tested.

Considering that spores of many diverse organisms have common physical and functional properties, it is expected that the various embodiments of the present invention will function well with spores prepared from different spore-forming species including bacteria, fungi, plants, and yeast.

Table 2 lists several spore-forming bacteria and corresponding germinants. It should be noted that mutants of spore-forming organisms in which the specificity of the germinant receptor has been altered can also be phenotypically engineered using the inventive method.

TABLE 2

| Spore forming bacteria and corresponding spore germinants | |
|---|---|
| Bacteria | Germinant |
| *Bacillus atrophaeus* | L-alanine |
| *Bacillus anthracis* | L-alanine + inosine |
| *Bacillus cereus* | L-alanine + adenosine |
| *Bacillus licheniformis* | Glucose, Inosine |
| *Bacillus megaterium* | Glucose, L-proline, KBr |
| *Geobacillus stearothermophilus* | Complex medium (TSB broth) |
| *Bacillus subtilis* | L-alanine |

Detection: Many of the embodiments of the present invention employ fluorescence detection of spore germination. Detection can be accomplished through the use of spores producing colored, fluorescent, luminescent, or phosphorescent enzymatic products during germination. In an embodiment employing a previously described biosensor (U.S. Pat. No. 6,872,539, Rotman), a charge-coupled device (CCD) readout can be used for imaging the response of the system to the analyte in the form of discrete luminescent microwells randomly distributed throughout the biosensor.

EXAMPLES

The following non-limiting example embodiments provide results that demonstrate the effectiveness of using phenotypic engineered spores for biosensing and sterility testing. All parts and percentages are by weight unless otherwise specified.

Example Embodiment 1

Detection of *Escherichia coli* Containing β-Lactamases
Detection of bacteria containing β-lactamases (EC 3.5.2.6) is clinically important because β-lactamases are usually good markers of bacterial resistance to β-lactam antibiotics. This example illustrates an application of the invention in the LEXSAS™, a biosensing system previously used for detecting low levels of bacteria in near real time (U.S. Pat. No. 6,872,539, Rotman; and Rotman, B. and Cote, M. A. Application of a real time biosensor to detect bacteria in platelet concentrates. (2003) Biochem. Biophys. Res. Comm., 300:197-200). Using self-reporting, fluorogenic, phenotypic engineered spores in the LEXSAS™ allows the LEXSAS™ to function more efficiently than other systems in which normal spores were used as detectors.

Enzymatic Production of Germinant: In this example, *E. coli* cells (the analyte) produce L-alanine (the germinant) by cleavage of L-alanyl deacetylcephalothin according to the following reaction:

$$\text{L-alanyl deacetylcephalothin} + \text{H}_2\text{O} \xrightarrow{\beta\text{-lactamase}} \text{L-alanine} + \text{deacetylcephalothin} \quad (1)$$

Spores: Spores derived from *B. cereus* 569H (ATCC 27522), a strain with constitutive β-lactamase II, were used. The spores require mixtures of amino acids and nucleosides for germination, e.g., L-alanine plus adenosine. The spores were obtained by growing bacteria in sporulation agar medium (ATCC medium No. 10) at 37° C. for 1-4 days. The spores were harvested with cold deionized water, heated at 65° C. for 30 min (to kill vegetative cells and to inactivate enzymes) and washed three or more times with deionized water. If necessary, the spores may be further purified according to conventional methodologies such as sonication, lysozyme treatment, and gradient centrifugation (Nicholson, W. L., and Setlow, P. (1990). Sporulation, germination, and outgrowth, p. 391-450, in C. R. Harwood and S. M. Cutting (ed.), Molecular biological methods for *Bacillus*. John Wiley & Sons, Sussex, England). After spore purification, the spores are resuspended in sterile, deionized water and stored at 40° C. Spore suspensions give satisfactory results after storage at this temperature for up to eight months. Alternatively, the spores may be lyophilized for longer storage.

For phenotypic engineering, about $3\times10^7$ spores were first dried under vacuum at room temperature, and then resuspended in 35 μL of acetone containing 1.0 mg/mL dipropionylfluorescein. The spore suspension was stirred for about one minute, and then the acetone was eliminated by evaporation under vacuum at room temperature. The resulting phenotypic engineered spores were resuspended in 100 mM TRIS-20 mM NaCl, pH 7.4, and washed twice in the same buffer.

Reaction mixture: Assays are set up in 96-well microtiter plates. Each well receives 0.18 mL of *B. cereus* engineered spores ($5\times10^7$ spores per mL) suspended in 100 mM sodium phosphate buffer, pH 7.2, containing 2 mM adenosine and 50 mM L-alanine deacetylcephalothin, the germinogenic substrate. This substrate is a $C_{IO}$ alanyl ester of deacetylcephalothin liberating L-alanine upon enzymatic hydrolysis of the β-lactam ring according to reaction (1). Synthesis of the substrate has been previously described by Mobashery S, and Johnston M. Inactivation of alanine racemase by β-chloro-L-alanine released enzymatically from amino acid and peptide $C_{IO}$-esters of deacetylcephalothin. (Biochem. 26:5878-5884 (1987)). Test samples (20 μL) containing a bacterial analyte (for example, *E. coli* K-12 (ATCC 15153) cells) are dispensed into each well, and the plate is incubated at 37° C. The number of tested bacterial cells in the sample may vary from 30 to 10,000. Using a microtiter plate fluorometer, fluorescence (excitation at 488 nm, emission at 520 nm) of individual wells is recorded at zero time and at 2-min intervals. Under these conditions, *E. coli* cells trigger appearance of fluorescence due to the following interconnected reactions:

(1) *E. coli* β-lactamase hydrolyses the germinogenic substrate ($C_{IO}$ L-alanyl deacetylcephalothin) liberating L-alanine, which, in turn, induces germination in phenotypic engineered, fluorogenic spores surrounding the *E. coli* cells;

(2) Germination of the engineered spores promotes release of fluorescent products from the spores;

(3) The course of the reaction is measured fluorometrically.

Appropriate positive and negative controls are included in the test.

Example Embodiment 2

Detection of *Pseudomonas aeruginosa* by Aminopeptidase Activity

This is another example embodiment illustrating the use of the invention in the LEXSAS™. The bacterial analyte is *P. aeruginosa* (ATCC 10145), a well-known human pathogen.

Enzymatic Production of Germinant: In this example, cells of *P. aeruginosa* (the analyte) have aminopeptidases producing L-alanine (the germinant) by hydrolysis of L-alanyl-L-alanine (Ala-Ala), a germinogenic dipeptide that does not induce spore germination by itself. Aminopeptidases belong to an extended family of enzymes that is present in practically all bacterial species and accordingly are considered universal bacterial markers. The biosensor response to bacterial analytes is based on their generating L-alanine from Ala-Ala according to reaction (2).

aminopeptidase

L-alanyl-L-alanine+$H_2O$→ - - - →L-alanine (2)

Spores: Spores derived from *B. cereus* 569H (ATCC 27522) were prepared and engineered as indicated above for Example Embodiment 1, except that the fluorogenic molecular probe for the engineering was diacetylfluorescein.

Biosensor operation: When using phenotypic engineered spores (constructed according to this invention) in the LEXSAS™ the spores produce fluorescence in response to presence of bacteria, which in this example are cells of *P. aeruginosa*. Biosensing was performed using glass fiber disks (Whatman GF/A, 6.35 mm diameter) impregnated with a 12-μL volume from a 40-μL reaction mixture containing $4.5\times10^7$ phenotypic engineered spores of *B. cereus*, 100 mM TRIS-20 mM NaCl buffer, pH 7.4, 0.9 mM Ala-Ala, 0.47 mM adenosine (or inosine), and a variable number of *P. aeruginosa* (the analyte). Appropriate positive and negative controls were included in the test. The number of *P. aeruginosa* tested varied from 30 to 10,000 cells per sample. The disks were incubated in a moist chamber at 37° C. for 15 minutes. After incubation, fluorescence images of the disks were captured and quantified using an image analysis system previously described (Rotman, B. and MacDougall, D. E. 1995 Cost-effective true-color imaging system for low-power fluorescence microscopy. CellVision 2:145-150). Disk fluorescence is expressed as "sum of fluorescent pixels" measured inside a square region of 3,600 pixels in the image center. Typical results (Table 3) demonstrate that the LEXSAS™ operating with spores engineered according to this invention performs with a high signal-to-noise ratio.

TABLE 3

**Detection of *P. aeruginosa* in the LEXSAS ™**

| Disk Content | Relative Fluorescence (1) | Signal/Noise |
|---|---|---|
| *P. aeruginosa* | 22,144 +/− 1,727 | 14.6 |
| Control (no analyte) | 1,510 +/− 108 | |
| Positive Control (2) | 28,987 +/− 2,175 | |

(1) Average sum of fluorescent pixels per disk ± SD of the mean. Triplicate disks were used per sample.
(2) Phenotypic engineered spores germinated with a mixture of L-alanine and inosine.

Example Embodiment 3

Biological Indicators for Dry Heat Sterility Testing

In this example, the invention was used to monitor dry heat sterilization using preparations of fluorogenic spores of *B. atrophaeus* (ATCC 9372) engineered as indicated above.

Spores: Spores were derived from *B. atrophaeus* (ATCC 9372)—a strain commonly used as biological indicators for dry-heat sterilization. Normal spores were prepared as indicated above for Example Embodiment 1. The spores require L-alanine and inosine for germination. For constructing phenotypic engineered spores, normal spores were heated at 65° C. for 30 min., washed and resuspended in 100 mM Tris-NaCl buffer, pH 7.4. A sample of 200 µL of the spore suspension (in a 1.5-mL polyallomer Beckman tube) was mixed with 5 µL of dimethylsulfoxide (DMSO) containing 5 mg/mL dibutyryl fluorescein as fluorogenic substrate. The mixture was incubated at room temperature for 10 minutes, and then the spores were pelleted by centrifugation at 12,000×g for 5 minutes at 0° C., which in general can be done in a range of 0° C.-30° C. After removing the supernatant, the pellet was resuspended with 200 µL of buffer. The suspension was transferred to a new polyallomer tube and the spores were washed twice with sterile deionized water.

Biological indicator: To use the phenotypic engineered spores as biological indicators, about 3×10$^6$ spores were dried on glass fiber discs (Whatman GF/A, 6.35 mm diameter). The disks were exposed to dry heat at temperatures ranging from 140° C. to 160° C. for variable periods of time. After the sterilization process, spore germination was tested by adding 12 µL, of Luria broth (the germinant) to each disk, and incubating the disks in a moist chamber for 20 minutes at 37° C. After incubation, fluorescence images of the disks were captured using an image analysis system for measuring fluorescence of solid materials (Rotman, B. and MacDougall, D. E. (1995). Cost-effective true-color imaging system for low-power fluorescence microscopy. CellVision 2:145-150). The results shown in Table 4 demonstrate that the phenotypic engineered spores performed well as biological indicators because spores in discs exposed to inadequate sterilization conditions (e.g., 150° C. for 12 minutes) retained only partial ability to release fluorescent products in response to germination signals. Moreover, the data from this and other similar experiments indicate that biological indicators made of phenotypic engineered spores have D values comparable to that of normal spores.

TABLE 4

Dry Heat Sterility Testing

| Time (min) | Relative Fluorescence (I) | % "Killing" |
|---|---|---|
| 0 | 62,344 +/− 12,456 | 0 |
| 4 | 24,736 +/− 1,957 | 60 |
| 8 | 11,796 +/− 5,844 | 81 |
| 12 | 4,000 +/− 1946 | 94 |
| Dead Spores (2) | 0 | 100 |

(1) Average sum of fluorescent pixels per disk ± SD of the mean. Triplicate disks were used for each sample.
(2) Spores were killed by exposing disks to dry heat at 150° C. for 66 minutes.

Example Embodiment 4

Biological Indicators for Steam Heat Sterility Testing Constructed by In Situ Engineering of Spores In this example embodiment, this invention was used to construct in situ biological indicators for steam heat sterility testing.

Spores: Spores were derived from *G. stearothermophilus* (ATCC 12980)—a strain commonly used as biological indicators for steam-heat sterilization. Normal spores were prepared as indicated above for Example Embodiment 1. The spores were germinated in the presence of tryptic soy broth (TSB).

Biological indicator. About 1×10$^6$ spores suspended in 0.5 µL, of sterile deionized water were dried as a small spot on a rectangular strip of glass fiber paper (Whatman GF/A) 6×17 mm. After drying, the strip was exposed to steam heat in an autoclave (VWR Accusterilizer) set at 121° C. for variable periods of time. After sterilization, the spores on the strip were converted to phenotypic engineered spores by adding 20 µL of 100 mM TRIS20 mM NaCl, pH 7.4 buffer containing 32 µg dibutyryl fluorescein and 70.4 mM dimethylsulfoxide (DMSO). The strip was incubated at room temperature for 5 minutes, and then it was placed in a small glass container for development by lateral flow diffusion of a germinant solution for 30 minutes at 55° C. The germinant solution was Luria broth (LB) diluted in 100 mM TRIS-20 mM NaCl buffer, pH 7.4 enriched with 112 mM Lalanine. After development, fluorescence images of the strips were captured using an image analysis system for measuring fluorescence of solid materials (Rotman, B. and MacDougall, D. E. (1995). Cost-effective true-color imaging system for low-power fluorescence microscopy. Cell Vision 2:145-150). The data shown in Table 5 demonstrate that phenotypic engineered spores constructed directly on a paper strip perform satisfactorily as biological indicators. That is, the engineered spores are still capable of germinating and producing fluorescence after exposing them to an inadequate steam heat process (e.g., 2.5 minutes), but do not produce fluorescence after a 100% lethal sterilization process. The D-value of phenotypic engineered spores killed by steam sterilization was found to be similar or higher than that of normal spores, i.e., between 2 and 3 minutes.

TABLE 5

Phenotypic engineered spores as biological indicators for steam heat

| Time (min) | Relative Fluorescence (1) | % "Killing" |
|---|---|---|
| 0 | 65,084 +/− 31,231 | 0 |
| 15 | 0 +/− 0 | 100 |

(1) Average sum of fluorescent pixels per disk ± SD of the mean. Duplicate strips were used for each sample.

Example Embodiment 5

Using Phenotypic Engineered Spores for Cell-Based Biosensing of Biological Warfare Agents There is an urgent need for new technology capable of monitoring the environment for biological warfare agents in near real time. In this example, spores engineered according to the invention are used as living detecting components of a rapid cell-based biosensor for biological warfare agents. As in Example Embodiment 1, the biosensor operates via the LEXSAS™ except that in this case the analytes are not bacteria but biological warfare agents tagged with a germinogenic enzyme. For example, a target biological warfare agent—such as *Staphylococcus* enterotoxin B—can be tagged with a specific antibody covalently linked to alkaline phosphatase to become a suitable analyte.

Spores: Normal spores derived from *B. megaterium* (ATCC 14581) were prepared as indicated for Example I, and subsequently phenotypic engineered as indicated for Example Embodiment 3-except that Syto 9 (INVITROGEN™) was used as fluorogenic molecular probe. Syto 9 is a nucleic acid stain that increases its fluorescence about 50 times when contacted with either DNA or RNA (Haugland, R. P. 2005 The *Handbook—A Guide to Fluorescent Probes and Labeling Technologies.—Molecular Probes*, Eugene, Oreg., 10th edition). These spores are germinated specifically by monosaccharides such as D-glucose, D-fructose, D-mannose, and methyl β-D-glucopyranoside. When using *B. megaterium* spores in the LEXSAS™, suitable germinogenic substrates are, for example, lactose (hydrolyzed by β-galactosidases), sucrose (hydrolyzed by sucrase), glucose-1-phosphate and glucose-6-phosphate (both hydrolyzed by phosphatases).

Biosensor operation: Spores of a non-virulent strain of *B. anthracis* (Sterne strain) were used as subrogates of spores causing anthrax. The spores were first coated with a specific anti-*B. anthracis* rabbit IgG, and then captured on paramagnetic beads coated with protein A. After separating, washing and blocking the magnetic beads with normal goat IgG, the spores on the beads were exposed to a secondary specific anti-*B. anthracis* goat IgG labeled with alkaline phosphatase. This process of using two specific antibodies (or other ligands) binding different epitopes for capturing and tagging biological particles is often used to enhance selectivity of a test and also to reduce the baseline noise, and it is critical for achieving high levels of selectivity necessary to avoid false positives. At the end of the process, the phosphatase-labeled beads are magnetically separated and then introduced in a biosensor capable of detecting and quantifying individual magnetic beads. The biosensor is a passive microfluidic device fabricated by spin coating a 15-μm thick silicon nitride photoresist on a 13-mm diameter polycarbonate filter membrane with uniform 0.2 μm pores. Subsequently, the silicon layer is photolithographically etched to produce about 80,000 MICRO-COLANDER™@ diagnostic analyzers. A MICRO-COLANDER™ analyzer is a microscopic reaction chamber of five-picoliter ($5 \times 10^{-12}$ L) volume that drains through thousands of uniform pores located at the bottom of the chamber (U.S. Pat. No. 6,872, 539, Rotman). Consequently, the biosensor performs as a filtration and collection device for capturing, detecting and enumerating weaponized biological particles (WPBS). The fact that each MICRO-COLANDER™ analyzer functions as an independent biosensor provides for both single magnetic bead sensitivity and straight forward quantitative analysis because the number of fluorescent pores of the MICRO-COLANDER™ analyzer containing WBPs equals the number of WBPs in the sample. Fluorescent images of the biosensor collected and analyzed at time intervals provide quantitative data.

Example Embodiment 6

Biological Indicators for Ethylene Oxide Sterility Testing Constructed by In Situ Engineering of Spores In this example embodiment, this invention was used to construct in situ biological indicators for Ethylene Oxide ($Et_2O$) sterilization testing.

Spores: Spores were derived from *B. globigii*—a strain commonly used as biological indicators for $Et_2O$ sterilization. Normal spores were prepared as indicated above for Example Embodiment 1. The spores were germinated in the presence of Tryptic soy bean broth (TSB).

Biological indicator. About $1 \times 10^6$ spores suspended in 0.5 μL, of sterile deionized water were dried as a small spot on a rectangular strip of glass fiber paper (Whatman GF/A) $6 \times 17$ mm. After drying, the strip was exposed to $Et_2O$ in for variable periods of time. After sterilization, the spores on the strip were converted to phenotypic engineered spores by adding 20 μL of 100 mM TRIS20 mM NaCl, pH 7.4 buffer containing 32 μg dibutyryl fluorescein and 70.4 mM dimethylsulfoxide (DMSO). The strip was incubated at room temperature for 5 minutes, and then it was placed in a small glass container for development by lateral flow diffusion of a germinant (112 mM L-alanine) solution for 30 minutes at 37° C. After development, fluorescence images of the strips were captured using an image analysis system for measuring fluorescence of solid materials.

Example Embodiment 7

Self-Contained Biological Indicators for Vaporized Hydrogen Peroxide

In this example embodiment, engineered spores were used within Self-Contained Biological Indicators for monitoring vaporized hydrogen peroxide sterilization.

Spores: Spores were derived from *G. stearothermophilus* (ATCC 12980), a strain commonly used for biological indicators of sterilization. Normal spores were prepared as indicated above for Example Embodiment 1.

Self-Contained Biological indicator (SCBI): The SCBI comprises:
a) a vial containing a disc inoculated with engineered spores, comprising about $1 \times 10^6$ fluorogenic bacterial spores of *Geobacillus stearothermophilus* prepared according to Example Embodiment 1; and
b) a breakable ampoule inside the vial containing Tryptic soy bean broth (TSB) growth medium.

Operation: The SCBI is exposed to Vaporized Hydrogen Peroxide in a STERRAD NX sterilizer (Johnson & Johnson) for variable periods of time. After the sterilization process, the SCBI is analyzed in an autoreader that automatically breaks the ampoule, incubates the SCBI at 55° C. for 30 minutes, and captures sequential fluorescence images of the disk using an image analysis system for measuring fluorescence of solid materials (Rotman, B. and MacDougall, D. E. (1995). Cost-effective true-color imaging system for low-power fluorescence microscopy. Cell Vision 2:145-150). The data obtained using SCBIs demonstrate that the phenotypic engineered spores perform satisfactorily as biological indicators for Vaporized Hydrogen Peroxide. That is, the engineered spores are still capable of germinating and producing substantial fluorescence after exposing them to an inadequate Vaporized Hydrogen Peroxide process, but do not produce significant fluorescence after a 100% lethal sterilization process.

In an embodiment, as supported by the foregoing disclosure, an engineered spore can include a first spore, which is a natural spore, i.e. a spore in an unmodified state, as found in nature, which has been configured to incorporate a compound, which can be at least partially hydrophobic, wherein the compound has a visual generating property, such as:
- a. fluorogenicity, such that the compound has an inherent capability of generating fluorescence upon a specific activation, such as hydrolysis;
- b. chromogenicity, such that the compound has an inherent capability of generating a color upon a specific activation, such as hydrolysis;
- c. chemiluminogenicity, such that the compound has an inherent capability of generating light upon a specific activation that involves a chemical process;
- d. bioluminogenicity, such that the compound has an inherent capability of generating light upon a specific activation that involves a biochemical or biological process; and
- e. indigogenicity, such that the compound has inherent capability of generating insoluble indigo blue upon a specific activation, such as hydrolysis.

In an embodiment, as supported by the foregoing disclosure, an engineered spore, can include:
- a) a first spore; and
- b) an at least partially hydrophobic compound, which is incorporated into the first spore;
- wherein the at least partially hydrophobic compound is fluorogenic, such that the hydrophobic compound is configured to become fluorescent by hydrolysis;
- wherein the sole fluorogenic compound in the engineered spore is the at least partially hydrophobic compound that is incorporated into the first spore, such that there are no other fluorogenic compounds in the engineered spore than the at least partially hydrophobic compound that is incorporated into the first spore;
- wherein the engineered spore is configured to be capable of germination; and
- wherein the engineered spore is non-fluorescent;
- wherein the engineered spore does not comprise a germinant;
- such that the engineered spore is configured to become fluorescent upon germination.

In this context, it shall be understood that an at least partially hydrophobic compound is hydrophobic in at least a part of the compound, and can be one of:
- a) a hydrophobic compound, which is an entirely hydrophobic compound; or
- b) an amphiphilic compound, which includes a hydrophilic part and a hydrophobic part.

In a related embodiment, the at least partially hydrophobic compound, can comprise a plurality of different fluorogenic at least partially hydrophobic compounds. The at least partially hydrophobic compound can for example include a fluorogenic hydrophobic compound and a fluorogenic amphiphilic compound.

In a related embodiment, the at least partially hydrophobic compound can be the hydrophobic compound dipropionylfluorescein.

In another related embodiment, the at least partially hydrophobic compound can be the hydrophobic compound diacetyl fluorescein.

In yet a related embodiment, the at least partially hydrophobic compound can be the hydrophobic compound dibutyryl fluorescein.

In a related embodiment, the at least partially hydrophobic compound can be the amphiphilic compound SYTO 9.

In a related embodiment, the first spore can be a spore of *Geobacillus stearothermophilus*.

In a related embodiment, the first spore can be a spore of *Bacillus cereus*.

In a related embodiment, the first spore can be a spore of *Bacillus atrophaeus*.

In a related embodiment, the first spore can be a spore of *Bacillus megaterium*.

In an embodiment, as supported by the foregoing disclosure, a method of using engineered spores to test adequate sterility of a system, can include sterilizing the system together with the engineered spores, subsequently incubating the engineered spores with a germinant, and finally measuring fluorescence of the engineered spores; such that a fluorescence measurement above a predetermined zero-baseline value, i.e. above a substantially zero fluorescence measurement, indicates that the sterilization process is adequate, and a fluorescence measurement equal to or less than the predetermined zero-baseline level indicates that the sterilization process is inadequate.

In an embodiment, as supported by the foregoing disclosure, an engineered spore suspension, can include:
- a) a sterile liquid solution, which does not comprise any fluorogenic compound, and does not comprise any fluorescent compound; and
- b) a plurality of engineered spores, wherein each engineered spore includes:
  a first spore; and
  an at least partially hydrophobic compound, which is incorporated into the first spore;
- wherein the plurality of engineered spores is suspended in the sterile liquid solution;
- wherein the at least partially hydrophobic compound is fluorogenic, such that the at least partially hydrophobic compound is configured to become fluorescent by hydrolysis;
- wherein the sole fluorogenic compound in the engineered spore suspension is the at least partially hydrophobic compound that is incorporated into the first spore of each engineered spore, such that there are no other fluorogenic compounds in the engineered spore suspension than the at least partially hydrophobic compound that is incorporated into the first spore of each engineered spore;
- wherein the engineered spores are configured to be capable of germination; and
- wherein the engineered spores are non-fluorescent;
- wherein the engineered spore suspension does not comprise a germinant;
- such that the engineered spores are configured to become fluorescent upon germination.

In a related embodiment, the engineered spore suspension includes only the at least partially hydrophobic compound, which is solely incorporated in the plurality of engineered spores, such that the sterile liquid solution does not include any fluorogenic compound, and such that the sterile liquid solution does not include any fluorescent compound.

Figure 1:
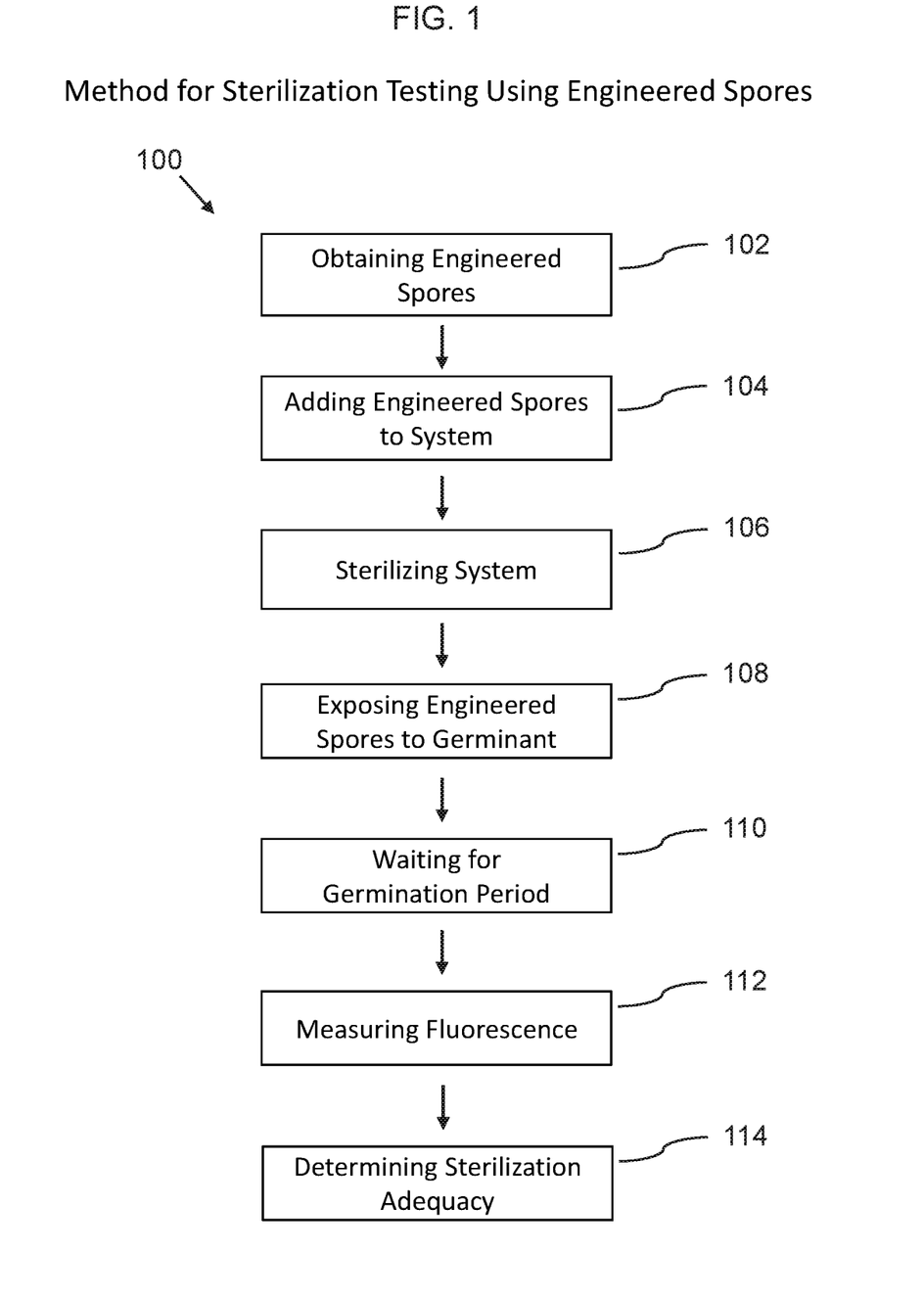

In an embodiment, as supported by the foregoing disclosure, and as illustrated in FIG. 1, a method of using engineered spores to test adequacy of a sterilization process for a system 100, can include:

a) obtaining the engineered spores 102, such as for example by manufacturing or procuring the engineered spores;

b) adding the engineered spores to the system 104, wherein the engineered spores are incorporated into, onto, or by a side of the system, for example by being dispersed in or on the system, by being injected into the system, or by being positioned on, in, or inside the system, or by being positioned adjacent to the system;

c) sterilizing the system 106, wherein the system with the engineered spores is subjected to the sterilization process;

d) exposing the engineered spores to a germinant 108, wherein the engineered spores are exposed to a germinant for a predetermined germination period 110, which can be in a range of 4-30 minutes;

e) measuring fluorescence 112, wherein the fluorescence of the engineered spores is measured to obtain a fluorescence measurement (which can also be called a fluorescence response or a fluorescence signal); and f) determining sterilization adequacy 114, such that if the fluorescence measurement is above a predetermined zero-baseline value, i.e. above a substantially zero fluorescence measurement, this indicates that the sterilization process is inadequate, and if the fluorescence measurement equal to or less than the predetermined zero-baseline level, this indicates that the sterilization process is adequate.

In a related embodiment, the zero-baseline value establishes a threshold for inherent noise and measurement errors, to distinguish between a substantially zero measurement, and a measurement that contains a valid indication of fluorescence. The fluorescence zero baseline level can for example be set to a relative fluorescence of 5,000 fluorescent pixels per disk.

Figure 2:
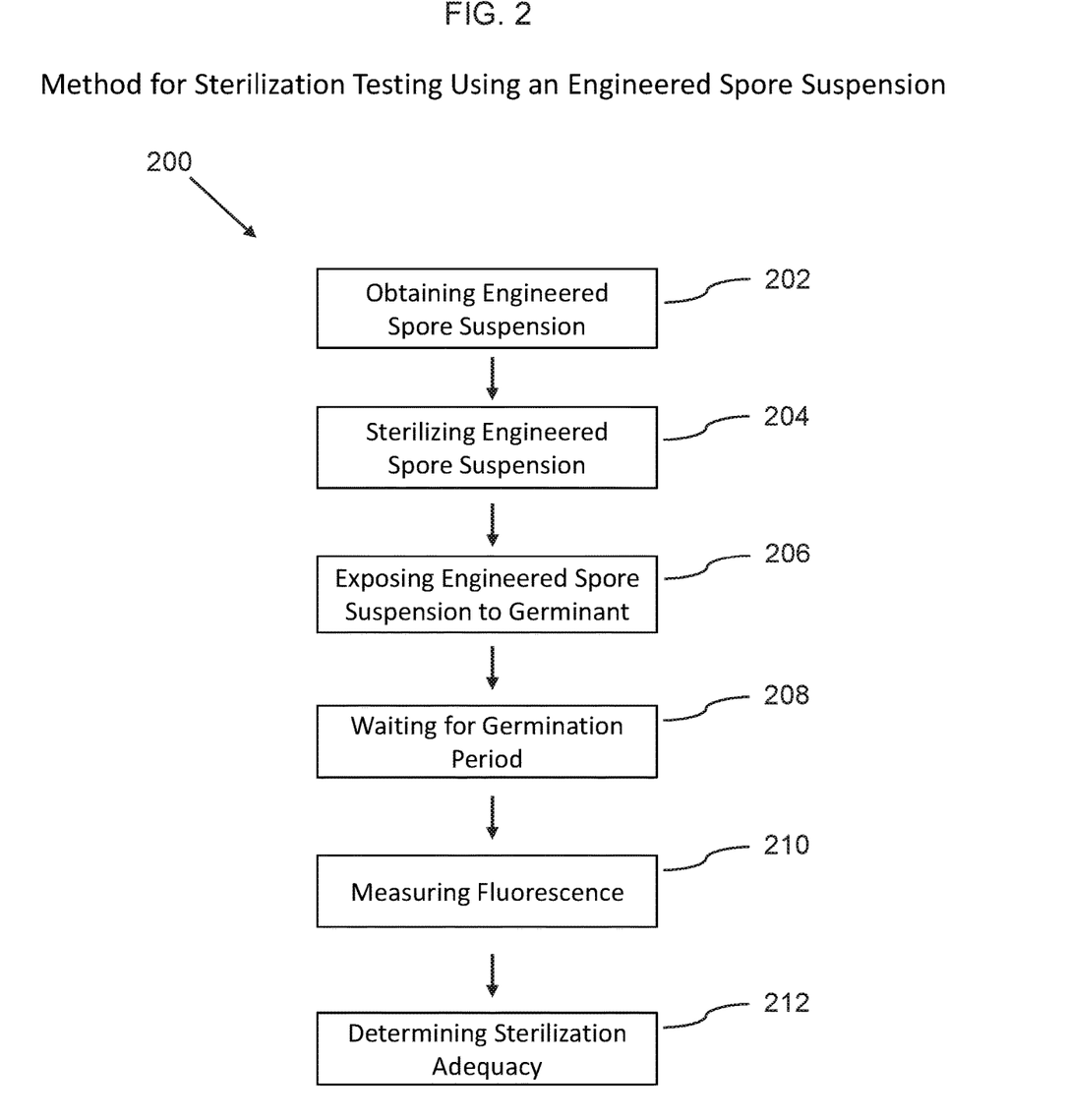

In an embodiment, as supported by the foregoing disclosure, and as illustrated in FIG. 2, a sterilization testing method 200 for testing the adequacy of a sterilization process, can include:

a) obtaining an engineered spore suspension 202;

b) sterilizing the engineered spore suspension 204, wherein the engineered spore suspension is subjected to the sterilization process;

c) incorporating a germinant into the engineered spore suspension 206;

d) waiting for a predetermined germination period 208, which can be in a range of 4-30 minutes;

e) measuring fluorescence 210, wherein the fluorescence of the engineered spore suspension is measured to obtain a fluorescence measurement; and f) determining sterilization adequacy 212, such that if the fluorescence measurement is above a predetermined zero-baseline value, i.e. above a substantially zero fluorescence measurement, this indicates that the sterilization process is inadequate, and if the fluorescence measurement equal to or less than the predetermined zero-baseline level, this indicates that the sterilization process is adequate.

wherein the engineered spore suspension comprises:
a sterile liquid solution; and
a plurality of engineered spores;
wherein the plurality of engineered spores is suspended in the sterile liquid solution.

Here has thus been described a multitude of embodiments of an engineered spore and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A method of using engineered spores to test adequacy of a sterilization process for a system, comprising:
    a) introducing the engineered spores into the system;
    b) sterilizing the system, wherein the system with the engineered spores is subjected to the sterilization process;
    c) exposing the engineered spores to a germinant for a predetermined germination period;
    d) measuring fluorescence, wherein the fluorescence of the engineered spores is measured to obtain a fluorescence measurement; and
    e) determining sterilization adequacy, such that:
        if the fluorescence measurement is above a predetermined zero-baseline value, the sterilization process is determined to be inadequate, and
        if the fluorescence measurement is equal to or less than the predetermined zero-baseline level, the sterilization process is determined to be adequate;
    wherein the engineered spores each comprise:
        a first spore; and
        an at least partially hydrophobic compound, which is incorporated into the first spore;
    wherein the at least partially hydrophobic compound is fluorogenic, such that the at least partially hydrophobic compound is configured to become fluorescent by hydrolysis;
    wherein a sole fluorogenic compound in the engineered spores is the at least partially hydrophobic compound that is incorporated into the first spore in each of the engineered spores;
    wherein the at least partially hydrophobic compound is present solely within the first spore in each of the engineered spores;
    wherein the engineered spore is configured to be capable of germination; and
    wherein the engineered spore is non-fluorescent;
    wherein the engineered spore does not comprise a germinant;
    such that the engineered spore is configured to become fluorescent upon germination.

2. The method of using engineered spores of claim 1, wherein the sterilization process is dry heat sterilization, such that sterilizing the system comprises exposing the system with the engineered spores to dry heat in a temperature range of 140-160 degrees Celsius.

3. The method of using engineered spores of claim 1, wherein the sterilization process is steam heat sterilization, such that sterilizing the system comprises exposing the system with the engineered spores to steam heat.

4. The method of using engineered spores of claim 1, wherein the first spore is selected from the group consisting of bacteria, fungi, plants, and yeast.

5. The method of using engineered spores of claim 1, wherein the at least partially hydrophobic compound is an entirely hydrophobic compound.

6. The method of using engineered spores of claim 1, wherein the at least partially hydrophobic compound is an amphiphilic compound.

7. The method of using engineered spores of claim 1, wherein the at least partially hydrophobic compound is dipropionylfluorescein.

8. The method of using engineered spores of claim 1, wherein the at least partially hydrophobic compound is diacetyl fluorescein.

9. The method of using engineered spores of claim 1, wherein the at least partially hydrophobic compound is dibutyryl fluorescein.

10. The method of using engineered spores of claim 1, wherein the at least partially hydrophobic compound is SYTO 9.

11. The method of using engineered spores of claim 1, wherein the first spore is a spore of *Geobacillus stearothermophilus*.

12. The method of using engineered spores of claim 1, wherein the first spore is a spore of *Bacillus cereus*.

13. The method of using engineered spores of claim 1, wherein the first spore is a spore of *Bacillus atrophaeus*.

14. The method of using engineered spores of claim 1, wherein the first spore is a spore of *Bacillus megaterium*.

15. A method of using engineered spores to test adequate sterility of a system, comprising sterilizing the system together with the engineered spores, subsequently incubating the engineered spores with a germinant, and finally measuring fluorescence of the engineered spores;

wherein the engineered spores each comprise:
a first spore; and
an at least partially hydrophobic compound, which is incorporated into the first spore;

wherein the at least partially hydrophobic compound is fluorogenic, such that the at least partially hydrophobic compound is configured to become fluorescent by hydrolysis;

wherein a sole fluorogenic compound in the engineered spores is the at least partially hydrophobic compound that is incorporated into the first spore in each of the engineered spores;

wherein the at least partially hydrophobic compound is present solely within the first spore in each of the engineered spores;

wherein the engineered spore is configured to be capable of germination; and wherein the engineered spore is non-fluorescent;

wherein the engineered spore does not comprise a germinant;

such that the engineered spore is configured to become fluorescent upon germination.

* * * * *